(12) United States Patent
Rudat

(10) Patent No.: US 9,347,174 B2
(45) Date of Patent: May 24, 2016

(54) AQUEOUS SILSESQUIOXANE DISPERSIONS HAVING LOW CONCENTRATIONS OF REACTION BYPRODUCTS

(71) Applicant: INVISTA North America S.a.r.l., Wilmington, DE (US)

(72) Inventor: Martin August Rudat, Woodstock, GA (US)

(73) Assignee: INVISTA North America S.a.r.l., Wilmington, DE (US)

( * ) Notice: Subject to any disclaimer, the term of this patent is extended or adjusted under 35 U.S.C. 154(b) by 424 days.

(21) Appl. No.: 13/798,363

(22) Filed: Mar. 13, 2013

(65) Prior Publication Data

US 2013/0260084 A1 Oct. 3, 2013

Related U.S. Application Data

(62) Division of application No. 12/722,264, filed on Mar. 11, 2010, now Pat. No. 8,420,734.

(60) Provisional application No. 61/159,825, filed on Mar. 13, 2009.

(51) Int. Cl.
| | |
|---|---|
| *D06M 13/513* | (2006.01) |
| *B82Y 30/00* | (2011.01) |
| *C07F 7/21* | (2006.01) |
| *C09C 1/30* | (2006.01) |
| *D06M 15/643* | (2006.01) |
| *D06M 23/08* | (2006.01) |

(52) U.S. Cl.
CPC .............. *D06M 13/513* (2013.01); *B82Y 30/00* (2013.01); *C07F 7/21* (2013.01); *C09C 1/3081* (2013.01); *D06M 15/643* (2013.01); *D06M 23/08* (2013.01); *C01P 2004/64* (2013.01); *C01P 2004/84* (2013.01); *Y10T 428/23986* (2015.04)

(58) Field of Classification Search
CPC ..... C07F 7/21; D06M 13/513; D06M 15/643; D06M 23/08; C09C 1/3081
USPC ........................................................ 252/8.62
See application file for complete search history.

(56) References Cited

U.S. PATENT DOCUMENTS

| | | | | |
|---|---|---|---|---|
| 3,620,823 | A * | 11/1971 | Smith ............................ | 427/387 |
| 3,986,997 | A * | 10/1976 | Clark ............................ | 524/300 |
| 4,355,135 | A * | 10/1982 | January ......................... | 524/767 |
| 4,617,057 | A * | 10/1986 | Plueddemann ................... | 106/2 |
| 6,225,403 | B1 * | 5/2001 | Knowlton ...................... | 524/858 |
| 7,915,368 | B2 * | 3/2011 | Hergenrother et al. .......... | 528/12 |
| 2003/0060395 | A1 * | 3/2003 | Chang et al. ................... | 510/460 |
| 2005/0227893 | A1 * | 10/2005 | Johnson et al. ............... | 510/367 |
| 2006/0115439 | A1 * | 6/2006 | Lu .................................. | 424/63 |
| 2008/0216709 | A1 * | 9/2008 | Steingrover et al. ...... | 106/287.11 |
| 2008/0287020 | A1 * | 11/2008 | Rudat ............................ | 442/94 |
| 2011/0144235 | A1 * | 6/2011 | Hergenrother et al. ........ | 523/156 |

* cited by examiner

*Primary Examiner* — Anthony J Green
(74) *Attorney, Agent, or Firm* — Joseph N. Moonjely

(57) ABSTRACT

Methods of making a composition are disclosed, which comprises: i) forming a dispersion of particles comprising: a) silica, b) a non-volatile cation, and c) water, wherein the non-volatile cation is not ammonium; ii) adding at least one organosilyl coupling agent of formula $R_1$—$(R_2$—$O)_3$—Si where $R_1$ is selected from the group consisting of a substituted alkyl and unsubstituted alkyl, and $R_2$ is selected from the group consisting of methyl, ethyl, propyl and butyl, wherein the substituted alkyl of $R_1$ is not aminoalkyl; iii) reacting the organosilyl coupling agent with the dispersion of particles to form a mixture comprising a silsesquioxane and an alcohol; and iv) removing the alcohol from the mixture by vacuum distillation, wherein final concentration of the alcohol is about 1% by weight or less of the total mixture. Further disclosed are compositions comprising an aqueous dispersion comprising silsesquioxane, a non-volatile cation and an alcohol, and methods of using the composition.

5 Claims, No Drawings

AQUEOUS SILSESQUIOXANE DISPERSIONS HAVING LOW CONCENTRATIONS OF REACTION BYPRODUCTS

CROSS-REFERANCE TO RELATED APPLICATIONS

This application is a division of U.S. patent application Ser. No. 12/722,264, filed Mar. 11, 2010, now U.S. Pat. No. 8,420,734, which claims benefit of priority from U.S. Provisional Application No. 61/159,825, filed Mar. 13, 2009.

FIELD OF THE INVENTION

The present invention relates to a silsesquioxane dispersion having distinctively low concentrations of volatile alcohol reaction byproducts suitable for application to carpets and other textiles.

BACKGROUND OF THE INVENTION

Silsesquioxane dispersions have been found to be useful for treatment of carpets and textiles in concert with fluorochemical resins to impart oil and water repellency and general resistance to soil as disclosed in U.S. Pat. No. 6,225,403 (Knowlton). However, where such dispersions are produced by condensation reactions using alkyltrialkoxysilanes, unacceptably large amounts of alkoxy compounds (for example methanol in the case of alkyltrimethoxysilanes) may be present as a byproduct of the silane reaction. Alkoxy compounds such as methanol are generally undesirable in treatment compositions and on treated articles but cannot be removed effectively during the condensation reaction process since the silanes are sufficiently volatile that a removal process is likely to remove the desired reactant as well. Upon completion of the reaction, the usual methods of cleaning and re-dispersing the silsesquioxane particles are cumbersome and are likely to result in extensive and undesirable agglomeration of the reaction products and consequent loss of both effectiveness and yield.

Surface-modified silica dispersions that have been produced by condensation reactions with alternative reagents result in alternative byproducts which are also undesirable, examples being triethoxysilanes yielding ethanol, and halogenated silanes yielding halogen acids. Halogen acids can cause undesirable agglomeration owing to related changes in pH, while ethanol is undesirable for articles such as carpet because, like methanol, it is a volatile organic compound.

Several methods are potentially useful to remove the above mentioned alcohol reaction byproducts from water. However, it has been found that many are unsuitable when applied to silsesquioxane dispersions of the kind applicable to carpets and textiles. In particular, it has been found that undesirable agglomeration of silsesquioxane dispersions results when evaporation is employed to remove either methanol or ethanol from such systems. Dispersions that are particularly applicable to carpets and textiles have typically been formed in aqueous systems buffered with ammonium counter-ions to stabilize them. The ammonium-ammonia equilibrium may be adversely affected by evaporation, so that the resulting system may no longer support the dispersion of all of the particles, and precipitation of some or all of the suspended particles of the dispersion may ensue. It has also been observed that silsesquioxane dispersions built from silica cores suffer from the same issues that are encountered with the surface-modified silica dispersions.

U.S. patent application number 2008/0216709A1 (Steingrover) teaches that acidic aminoalkylsilane modified silica particles are stable in acidic aqueous solutions in contrast to other alkylsilane materials. However, the organic amine functionality disclosed by Steingrover is not capable of creating hydrophobic, soil resistant and oil repellent fabrics.

SUMMARY OF THE INVENTION

Therefore, there is a need for an efficient and effective route to remove dissolved byproducts as described above from silsesquioxane dispersions while maintaining the stability of the dispersion.

In accordance with the present invention, changes to the method of formation of certain silsesquioxane dispersions allow efficient and effective removal of dissolved byproducts in the silsesquioxane dispersions while maintaining the stability of the dispersion. Specifically, a generally hydrophobic silsesquioxane dispersion that includes a non-volatile free cation is stable to vacuum distillation. Sodium stabilized surface-modified silica particles or silica-core silsesquioxanes, for example, tolerate vacuum distillation of byproducts like methanol to a very low level, the level determined by a combination of vacuum level, temperature, stirring, and time.

In one aspect, a method of making a composition is disclosed, which comprises: i) forming a dispersion of particles comprising: a) silica, b) a non-volatile cation, and c) water, wherein the non-volatile cation is not ammonium; ii) adding at least one organosilyl coupling agent of formula $R_1$—$(R_2$—$O)_3$—Si where $R_1$ is selected from the group consisting of a substituted alkyl and unsubstituted alkyl, and $R_2$ is selected from the group consisting of methyl, ethyl, propyl and butyl, wherein the substituted alkyl of $R_1$ is not aminoalkyl; reacting the organosilyl coupling agent with the dispersion of particles to form a mixture comprising a silsesquioxane and an alcohol; and iv) removing the alcohol from the mixture by vacuum distillation, wherein final concentration of the alcohol is about 1% by weight or less of the total mixture. The present invention further relates to a composition comprising a silsesquioxane, a non-volatile cation and an alcohol, and methods of using the composition.

In another aspect, a composition is disclosed, which comprises an aqueous dispersion comprising a silsesquioxane, a non-volatile cation and an alcohol, wherein the concentration of alcohol is about 0.5% by weight or less of the total composition and wherein the non-volatile cation is not ammonium.

In a further aspect, a method of treating carpet is disclosed, which comprises applying a composition comprising an aqueous dispersion comprising a silsesquioxane, a non-volatile cation and an alcohol, wherein the concentration of alcohol is about 0.5% by weight or less of the total composition and wherein the non-volatile cation is not ammonium to the carpet and drying the carpet.

DETAILED DESCRIPTION OF THE INVENTION

Disclosed is a method of making a composition comprising: i) forming a dispersion of particles comprising: a) silica, b) a non-volatile cation, and c) water, wherein the non-volatile cation is not ammonium; ii) adding at least one organosilyl coupling agent of formula $R_1$—$(R_2$—$O)_3$—Si where $R_1$ is selected from the group consisting of a substituted alkyl and unsubstituted alkyl, and $R_2$ is selected from the group consisting of methyl, ethyl, propyl and butyl, wherein the substituted alkyl of $R_1$ is not aminoalkyl; iii) reacting the organosilyl coupling agent with the dispersion of particles to form a mixture comprising a silsesquioxane and an alcohol; and iv) removing the alcohol from the mixture by vacuum distillation, wherein final concentration of the alcohol is about 1% by weight or less of the total mixture. Optionally, the final concentration of the alcohol can be about 0.5% by weight or less of the total mixture, including about 1000 ppm or less of the total mixture. The dispersion can also be referred to as a sol. The composition made by this method can be used in fabric treatment, including treating carpets A combination of temperature and pressure is used for vacuum distillation to remove the alcohol. The temperature can be between from about 30° C. and about 80° C., including from about 40° C. to about 60° C., and from about 40° C. to about 50° C. The distillation temperature can also be about 40° C. and about 45° C. The vacuum applied during distillation is less than 200 torr, including less than 150 ton, less than 100 torr, less than 75 torr, and about 50 torr. The vacuum applied can also be in the range from about 75 torr to about 50 torr, including about 75 torr. One combination of temperature and pressure to remove the alcohol is about 45° C. and about 75 ton.

The non-volatile cation can be selected from alkaline metals, for example the group consisting of lithium, sodium, potassium, and cesium. Divalent non-volatile cations, for example magnesium and calcium, can be employed in the process of the present invention but they may have a propensity to interact (form precipitates) with other chemicals subsequently added or combined with the resultant composition. The non-volatile cation of the present invention is not ammonium. $R_2$ can be selected from the group consisting of methyl, ethyl and propyl. $R_1$ can be selected from the group consisting of methyl, ethyl, propyl and butyl, or $R_1$ can be a haloalkyl. The substituted alkyl of $R_1$ is not aminoalkyl.

The disclosed method can further comprise v) mixing the product produced in step iv) with an aqueous dispersion comprising a fluorochemical resin. Additionally, the disclosed method can further comprise vi) applying the product of step v) to a carpet or fabric.

Also disclosed is a composition comprising a silsesquioxane, a non-volatile cation and an alcohol, wherein the concentration of alcohol is about 1% by weight or less of the total composition and wherein the non-volatile cation is not ammonium. The concentration of alcohol can be about 0.5% by weight or less of the total composition, including about 1000 ppm or less of the total composition. The composition can further comprise a fluorochemical resin; and optionally a carpet or fabric wherein the concentration of alcohol is about 100 ppm or less of the total carpet or fabric weight, including about 10 ppm or less of total carpet or fabric weight.

Further disclosed is a method of treating a carpet comprising, applying the above composition to the carpet and drying the carpet. The treated carpet can comprise an alcohol concentration of about 10 ppm or less of total carpet weight.

The disclosed method creates a silsesquioxane, surface-modified silica, and silica-core silsesquioxane particles as well as other materials with reactive silicon-based chemical groups made or modified using reactive silanes of the general formula $R_1$—$(R_2$—$O)_3$—Si where $R_1$ carries the desired surface chemistry functionality of the final particles or material and can be a substituted or unsubstituted alkyl chain, monomer, or polymer, and $R_2$ is a short-chain alkyl group ($R_2$ is generally the same for all three oxygen-containing pendant groups represented here, but may be different). The result of the reactions of interest is the liberation of $R_2$—OH into the medium. The medium can also contain one or more agents to effect a stable dispersion of the original particles (in the case in which silica or other particles are used as the starting material) or to support the formation and dispersion of the particles being formed.

One method to create aqueous particle dispersions is to combine charged particles with counter-ions. Anionically-charged particles are suitable in cases where attraction to a cationically charged substrate is desired or where dictated by the charge of other particles or chemicals in a solution.

For products that are to be used in aqueous media, water can be a suitable reaction medium. This avoids removal of undesired solvents, recovery of reaction products, and subsequent dispersion of the recovered products into water. In the case where the desired product is an aqueous dispersion of micro-and nanoparticles, creation of such particles in non-aqueous media with separation from the reaction solvent and subsequent dispersion in water without agglomeration or precipitation can be especially difficult without the addition of surfactants. Unfortunately, such surfactants compromise the efficacy of products to make carpets and textiles more hydrophobic and soil resistant.

Therefore, when water is used in reactions between silicates and organosilanes, the byproduct alcohol (methanol, ethanol, etc.) becomes dispersed in water. With the presence of the byproduct alcohol (and possibly other low-molecular weight impurities) volatile organic carbon (VOC) content may limit the ultimate usage of the final article or product.

As described above, creation of a dry powder and re-dispersion in water can be an available route that would result in the elimination of the VOC content, but agglomeration, precipitation, and cost are obstacles. Vacuum distillation can be used to remove volatile contaminants from solutions or dispersions from the mixture. However, some byproducts or impurities have an affinity for the medium that limits the amount which can be removed, such as when an azeotrope is formed.

Ammonium has been conventionally used as a counter-ion for anionically charged particles as it is compatible with many formulations and applications, and it provides some control of pH. It has been observed that application of the vacuum distillation method, with or without heating and/or stirring, fails when used with ammonium-stabilized silsesquioxane particle systems that are not otherwise supported, for example, by surfactants or other stable dispersing agents. For many applications, however, the additional material of such stabilizing agents is deemed undesirable. Among such applications, practical examples include the silsesquioxane particle systems appropriate to anti-soiling formulations for carpet, because the stabilizing agents tend to be chemically compatible with water, oil and dirt.

In one aspect of the disclosed method, the problem of byproduct alcohol contamination in silsesquioxane dispersions has been solved by using a non-volatile counter-ion (not ammonium) to stabilize the aqueous dispersion while methanol is removed through a process of vacuum distillation. In the case of the anionic silsesquioxane particles described above, the ammonium counter-ions can be replaced with sodium counter-ions. Since sodium ions are retained during vacuum distillation, the charge-stabilized dispersion is not disrupted and the dispersion remains stable throughout the process and in subsequent storage. Other counter-ions can include lithium, potassium, cesium, magnesium and calcium.

Methanol is effectively and efficiently removed even from relatively unstable hydrophobic silsesquioxane dispersions by applying vacuum distillation with mild heating. Under similar conditions, a large fraction of ethanol or propanol can be removed if ethoxy or propoxy silanes were used as reactants. Other relatively volatile byproducts can also be removed at the same time. The extent to which the byproducts and other volatiles are removed is dependent upon the specific conditions utilized (temperature, vacuum, and time). In all cases, the result is a stable dispersion with a substantially reduced concentration of volatile organic compounds remaining.

Methods are described where methanol is reduced from an initial concentration level of over 1% by weight to as little as 100 ppm or less in a single step process.

It is to be understood that various combinations of temperature, stirring, vacuum level, and time can be employed to enable the distillation of methanol or other alcoholic byproducts from reaction mixtures which may initially contain various concentrations of such alcohol, from as little as 0.1% to as much as 10% or more by weight, to achieve a desired resultant concentration. Depending on the intended use, residual methanol concentration may be reduced to less than about 10,000 ppm, or may be reduced to even less than 100 ppm. Levels as low as 20 ppm are achievable by further adjusting the conditions (higher temperature, improved vacuum, and/or longer time). Also disclosed is a sodium stabilized dispersion of alkylsilated silica which contains approximately 0.9% to 5% methanol that can be reduced to about 500 ppm methanol, including less than about 150 ppm methanol.

EXAMPLES

Test Methods

The amount of alcohol byproduct present in the aqueous dispersion before and after the vacuum distillation process was determined using gas chromatography with mass spectral detection (GC-MS). The residual alcohol in the dispersion was preferentially removed by extraction with ethyl acetate. The extract was filtered to remove particulates and the relative concentration of methanol was determined by GC-MS in comparison with known standards by the conventional method of standard additions.

Comparative Example 1

Approximately 1.2 kg of Ludox AS-40, from GraceDavidson, described as an ammonium stabilized suspension of silica particles in water that is approximately 40% by weight silica, with an average particle diameter of about 20 to 30 nm and a nominal pH of 9, was placed in a 20-Liter reactor. The particle suspension was slowly reacted with 30 g of methyltrimethoxysilane at about 30° C., to create an aqueous suspension of alkylsilane modified particles, which can be called silica-core silsesquioxanes, having a concentration of about 1% by weight of methanol. Slow stirring was maintained at about 40° C. and vacuum was applied to achieve about 50 torr pressure for about four hours to gradually remove the methanol. Significant precipitation solids were found, indicating agglomeration of particles and initiation of the breakdown of the stable particle dispersion.

Example 2

Approximately 1.2 kg of Ludox TM-40, from GraceDavidson, described as a sodium stabilized suspension of silica particles in water that is approximately 40% by weight silica, with an average particle diameter of about 20 to 30 nm and a nominal pH of 9, was placed in a 20-Liter reactor. The particle suspension was slowly reacted with 30 g of methyltrimethoxysilane at about 30° C., to create an aqueous suspension of alkylsilane modified particles, called silica-core silsesquioxanes, having a concentration of about 1% by weight of methanol. Slow stirring was maintained at about 40° C. and 50 ton pressure, gradually removing the methanol. After about 10 hours, less than 100 ppm of methanol was found to remain in solution. Little agglomeration of particles was observed.

While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims.

What is claimed is:

1. A composition consisting essentially of a) an aqueous dispersion consisting essentially of a silsesquioxane, a non-volatile cation and an alcohol, wherein the concentration of alcohol is about 0.5% by weight or less of the total composition and wherein the non-volatile cation is not ammonium, and b) a fluorochemical resin.

2. The composition of claim 1 wherein the concentration of alcohol is bout 1000 ppm by weight or less of the total composition.

3. The composition of claim 1 wherein the concentration of alcohol is about 200 ppm or less of the total composition.

4. A method of treating a carpet comprising applying the composition of any one of claim 1-3 to the carpet and drying the carpet.

5. A carpet produced by the method of claim 4, comprising an alcohol concentration of about 0.1 ppm or less of total carpet weight.

* * * * *